US012802757B2

(12) United States Patent
Eno et al.

(10) Patent No.: US 12,802,757 B2
(45) **Date of Patent: *Nov. 17, 2026**

(54) SEQUENCE ALIGNMENT WITH MEMORY ARRAYS

(71) Applicant: MICRON TECHNOLOGY, INC., Boise, ID (US)

(72) Inventors: Justin Eno, Boise, ID (US); Sean S. Eilert, Boise, ID (US); Ameen D. Akel, Boise, ID (US); Kenneth M. Curewitz, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 114 days.

This patent is subject to a terminal disclaimer.

(21) Appl. No.: 18/999,983

(22) Filed: Dec. 23, 2024

(65) Prior Publication Data

US 2025/0124981 A1 Apr. 17, 2025

Related U.S. Application Data

(63) Continuation of application No. 17/931,277, filed on Sep. 12, 2022, now Pat. No. 12,217,796.

(51) Int. Cl.
*G11C 13/00* (2006.01)
*C12Q 1/6869* (2018.01)
(Continued)

(52) U.S. Cl.
CPC ........ *G11C 13/0069* (2013.01); *C12Q 1/6869* (2013.01); *G11C 7/16* (2013.01); *G11C 13/004* (2013.01); *G16B 30/10* (2019.02)

(58) Field of Classification Search
CPC ..... G11C 13/0069; G11C 7/16; G11C 13/004; G11C 7/1006; G11C 13/0016; C12Q 1/6869; G16B 30/10; G16B 40/00
(Continued)

(56) References Cited

U.S. PATENT DOCUMENTS 9,741,399 B2 8/2017 Tiwari
9,947,376 B2 4/2018 Tiwari et al.
(Continued)

OTHER PUBLICATIONS

S. Gupta et al. "RAPID: A ReRAM Processing in-Memory Architecture for DNA Sequence Alignment", 2019 IEEE/ACM International Symposium on Low Power Electronics and Design (ISLPED), Lausanne, Switzerland, Jul. 29-31, 2019, pp. 1-6.
(Continued)

*Primary Examiner* — Huan Hoang
(74) *Attorney, Agent, or Firm* — Dorsey & Whitney LLP

(57) ABSTRACT

A memory device may be used to implement a Bloom filter. In some examples, the memory device may include a memory array to perform a multiply-accumulate operation to implement the Bloom filter. The memory device may store multiple portions of a reference genetic sequence in the memory array and compare the portions of the reference genetic sequence to a read sequence in parallel by performing the multiply-accumulate operation. The results of the multiply-accumulate operation between the read sequence and the portions of the reference genetic sequence may be used to determine where the read sequence aligns to the reference sequence.

20 Claims, 7 Drawing Sheets

(51) Int. Cl.
*G11C 7/16* (2006.01)
*G16B 30/10* (2019.01)

(58) Field of Classification Search
USPC .......................................................... 365/148
See application file for complete search history.

(56) References Cited

U.S. PATENT DOCUMENTS

| | | | | |
|---|---|---|---|---|
| 10,409,557 | B2 | 9/2019 | Tiwari | |
| 10,528,643 | B1 * | 1/2020 | Choi | G06F 17/16 |
| 12,073,110 | B2 | 8/2024 | Eno et al. | |
| 12,217,796 | B2 | 2/2025 | Eno et al. | |
| 2021/0074382 | A1 | 3/2021 | Van Aggelen | |
| 2021/0295949 | A1 | 9/2021 | Kinney | |
| 2021/0349837 | A1 | 11/2021 | Huangfu et al. | |
| 2024/0086100 | A1 | 3/2024 | Eno et al. | |
| 2024/0087643 | A1 | 3/2024 | Eno et al. | |

OTHER PUBLICATIONS

U.S. Appl. No. 17/931,262 titled, “Sequence Alignment With Memory Arrays” filed Sep. 12, 2022, pp. all pages of application as filed.
U.S. Appl. No. 17/931,277 titled, “Sequence Alignment With Memory Arrays” filed Sep. 12, 2022, pp. all pages of application as filed.
U.S. Appl. No. 17/006,602, titled “Bayesian Network in Memory”; filed Aug. 28, 2020; pp. all pages of application as filed.
V. Akhlaghi et al. “Restive Bloom Filters: From Approximate Membership to Approximate Computing with Bounded Errors”, 2016 Design, Automation & Test in Europe Conference & Exhibition, Dresden, Germany, Mar. 14-18, 2016; pp. 1441-1444.

* cited by examiner

SEQUENCE ALIGNMENT WITH MEMORY ARRAYS

CROSS REFERENCE TO RELATED APPLICATION(S)

This application is a continuation of U.S. patent application Ser. No. 17/931,277 filed Sep. 12, 2022 and issued as U.S. Pat. No. 12,217,796 on Feb. 4, 2025. The aforementioned application, and issued patent, is incorporated herein by reference, in its entirety, for any purpose.

BACKGROUND

Genetic information of an organism is stored in a genome which includes linear strings (e.g., sequences) of bases, referred to as nucleotides, which encode all of the instructions necessary for the organism. Common examples include deoxyribonucleic acid (DNA), which includes nucleotides adenine (A), guanine (G), cytosine (C), and thymine (T); and ribonucleic acid (RNA), which includes nucleotides A, C, G, but instead of T includes uracil (U). Determining the order of the nucleotides in the genome (e.g., the sequence), or portions thereof, is referred to as sequencing.

Determining a sequence of genetic information (e.g., a random DNA fragment, a gene, chromosome, entire genome) involves breaking the string of nucleotides into shorter strings and amplifying (e.g., replicating) the shorter strings. The sequences of the shorter strings are then determined, such as by tagging different nucleotides with different fluorescent markers and analyzing the fluorescent signals. However, other techniques for sequencing exist. Each sequence determined for a shorter string is referred to as a "read." These reads are analyzed and recombined (e.g., aligned) to provide the sequence of the longer string (e.g., the sequence of genetic information). In some cases, the reads may be aligned de novo to determine an unknown genetic sequence. In other cases, the reads may be aligned to a reference sequence.

When a reference sequence is used, the reads from a sample sequence are compared to the reference sequence to determine where the reads align to the reference sequence (e.g., alignment location). That is, at what location along the reference sequence the nucleotides of the read match the nucleotides of the reference sequence (if any). The reads may be aligned into the sample sequence based on where in the reference sequence the matches occurred. Or, if few or none of the reads had matches, it could be determined that the reads were from a sample that did not match the reference sequence. For example, a sample may be acquired from a patient, and reads from the sample may be compared to one or more reference sequences of one or more known pathogens (e.g., virus, bacteria). Based on the comparison of the reads to the reference sequences, it may be determined whether the patient is infected with one of the known pathogens. Thus, in some applications, aligning reads to a reference sequence may be used for diagnostic purposes.

Sequencing technologies, particularly next generation sequencing (NGS) systems, generate millions to billions of reads ranging anywhere from less than fifty nucleotides to more than a thousand nucleotides. Aligning these millions to billions of reads requires significant computation time. Accordingly, improved alignment techniques are desired.

DETAILED DESCRIPTION

As disclosed herein, a memory array may be used to implement a Bloom filter. The Bloom filter of the memory array may allow a read to be compared to many reference sequences or portions of reference sequences in parallel. The Bloom filter may provide an output indicating the read absolutely does not match the reference sequence or an output indicating the read may match the reference sequence. The possible matches may be compared to the read on a nucleotide-by-nucleotide basis or other technique to confirm which (if any) reference sequences the read matches. In some applications, the ability of the Bloom filter to compare the read to reference sequences in parallel and provide absolute negatives for matches (no match found) may reduce computation times for aligning reads to reference sequences, even when possible matches are further analyzed for confirmation of the match.

While memory devices have been traditionally seen as data storage devices that support computing devices, memories are increasingly being used as computing devices themselves. For example, memories have been configured to perform signed division and vector operations such as described in U.S. Pat. Nos. 9,741,399, 9,947,376, and 10,409,557, which are incorporated herein by reference for any purpose. In another example, memory arrays, such as resistive memory arrays, have been used to implement Bayesian networks for machine learning applications as described in U.S. patent application Ser. No. 17/006,602, which is incorporated herein by reference for any purpose. In some applications, utilizing memory arrays for certain computations may increase parallelization of the computations and/or reduce loads on a processor, a host system, and/or other computing device interacting with the memory.

Figure 1:
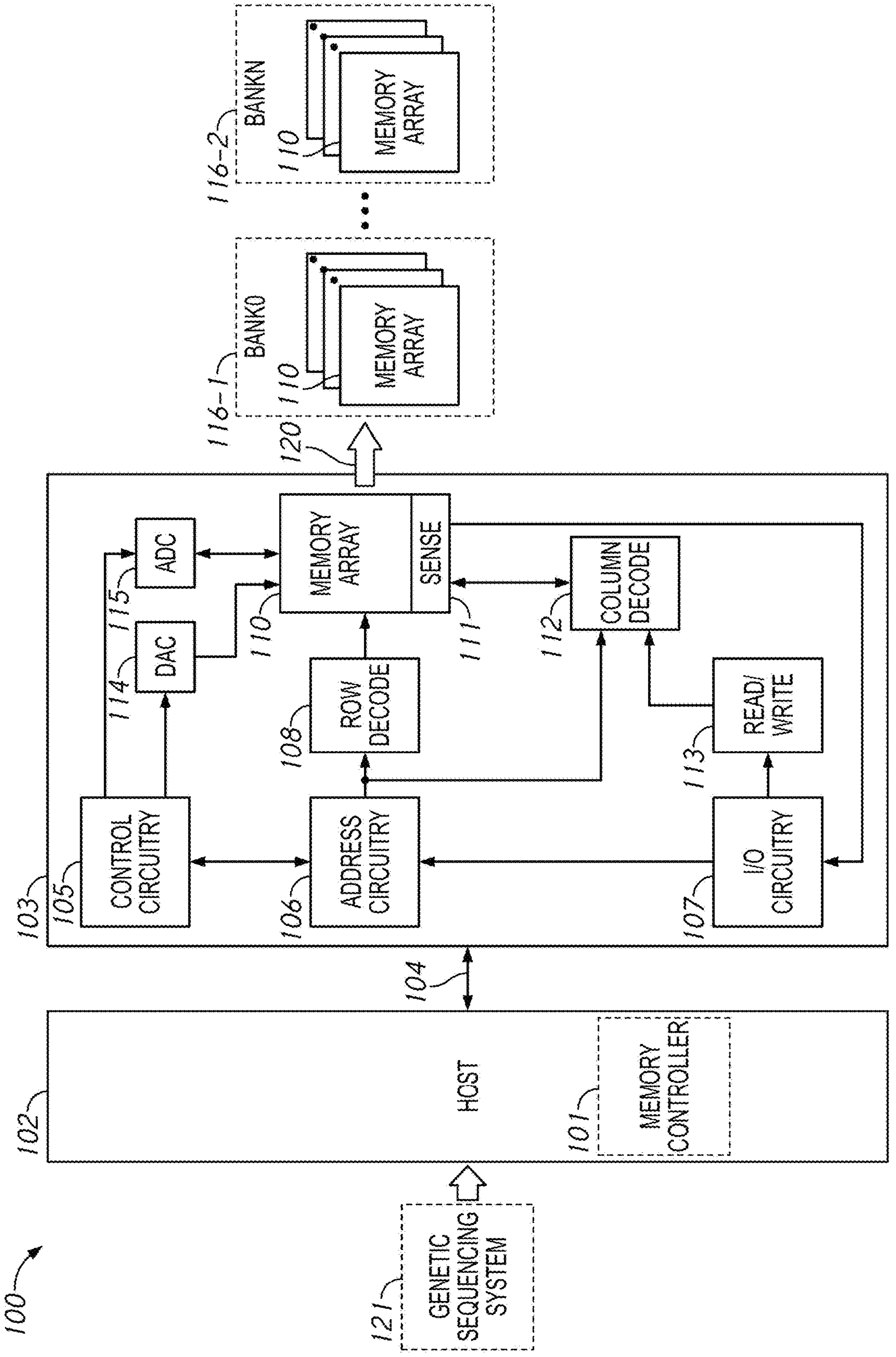
FIG. 1 is a block diagram of an apparatus in the form of a computing system including a memory device in accordance with a number of embodiments of the present disclosure.

FIG. 1 is a block diagram of an apparatus in the form of a computing system 100 including a memory device 103 in accordance with a number of embodiments of the present disclosure. As used herein, a memory device 103, memory array 110, and/or a host 102, for example, might also be separately considered an apparatus.

In this example, the computing system 100 includes a host 102 coupled to memory device 103 via an interface 104. The computing system 100 can be a personal laptop computer, a desktop computer, or an Internet-of-Things (IoT) enabled device, among various other types of computing devices and/or systems. In some examples, the system 100 may be in communication with or included in a system for genetic sequencing, such as a NGS system. In some examples, the host 102 may be included in a different device from the memory device 103. For example, host 102 may be included in genetic sequencing system 121 and the memory device 103 may be included in a separate computing device in communication with the genetic sequencing system 121. In some examples, the computing system 100 may be included in one or more computing devices in communication with the genetic sequencing system 121 (e.g., via host 102). Host 102 may include a number of processing resources (e.g., one or more processors, microprocessors, or some other type of controlling circuitry) capable of accessing memory device 103 (e.g., via one or more memory controllers 101). The computing system 100 may include separate integrated circuits, or both the host 102 and the memory device 103 may be on the same integrated circuit. For example, the host 102 may be a system controller of a memory system comprising multiple memory devices 103, with the system controller providing access to the respective memory devices 103 by another processing resource such as a central processing unit (CPU).

For clarity, the computing system 100 has been simplified to focus on features with particular relevance to the present disclosure. The memory array 110 may be a dynamic random access memory (DRAM) array, synchronous DRAM (SDRAM) array, spin-transfer torque (STT) RAM array, phase change (PC) RAM array, thyristor RAM (TRAM) array, resistive RAM array, NAND flash array, NOR flash array, and/or 3D cross-point array, for instance. The array 110 may include memory cells arranged in rows coupled by access lines (which may be referred to herein as word lines or select lines) and columns coupled by sense lines (which may be referred to herein as bit lines, digit lines or data lines).

Although the memory array 110 is shown as a single memory array, the memory array 110 may represent a plurality of memory arrays 110, which in some examples may be arranged in banks BANK0-BANKN 116-1, 116-2 of the memory device 103 as indicated by arrow 120. Each bank 116-1, 116-2 may include one or more memory arrays 110. Or conversely, memory array 110 may be organized into one or more banks, where each bank BANK0-BANKN includes a region of the memory array 110.

The memory device 103 includes address circuitry 106 to latch address signals provided over the interface 104. The interface 104 may include, for example, a physical interface employing a suitable protocol (e.g., a data bus, an address bus, and a command bus, or a combined data/address/command bus). Such protocol may be custom or proprietary, or the interface 104 may employ a standardized protocol, such as Peripheral Component Interconnect Express (PCie), Gen-Z interconnect, cache coherent interconnect for accelerators (CCIX), or the like. Address signals are received and decoded by a row decoder 108 and a column decoder 112 to access the memory arrays 110. Data may be read from memory arrays 110 by sensing voltage and/or current changes on the sense lines using sensing circuitry 111. The sensing circuitry 111 may be coupled to the memory arrays 110. Each memory array 110 and corresponding sensing circuitry 111 may constitute a bank of the memory device 103 in some examples. The sensing circuitry 111 may include, for example, sense amplifiers that may read and latch a page (e.g., row) of data from the memory array 110. The I/O circuitry 107 may be used for bi-directional data communication with the host 102 over the interface 104. The read/write circuitry 113 is used to write data to the memory arrays 110 or read data from the memory arrays 110. As an example, the circuitry 113 may include various drivers, latch circuitry, etc.

Control circuitry 105 decodes signals provided by the host 102. The signals may be commands provided by the host 102. These signals may include chip enable signals, write enable signals, and address latch signals that are used to control operations performed on the memory array 110, including data read operations, data write operations, and data erase operations. In various embodiments, the control circuitry 105 is responsible for executing instructions from the host 102. The control circuitry 105 may comprise a state machine, a sequencer, and/or some other type of control circuitry, which may be implemented in the form of hardware, firmware, or software, or any combination thereof. In some examples, the host 102 may be a controller external to the memory device 103. For example, the host 102 may be a memory controller which is coupled to a processing resource of a computing device, or alternatively host 102 may include one or more memory controllers 101. Data may be provided to the memory array 110 and/or from the memory array via the data lines coupling the memory array 110 to the I/O circuitry 107.

In various instances, the memory array 110 may be a resistive memory array. The resistive memory array may be a resistive programmable device. That is, the memory array 110 may be programmed by modifying the resistance of the memory cells of the memory array 110. The memory cells may be programed to a specific resistance and/or conductance. The resistance/conductance of the memory cells may represent values that can be used in the performance of operations. For instance, the conductance of the memory cells can be used to perform a multiplication operation, among other types of operations.

In various examples, the resistance of the memory cells can be programmed to represent nucleotides of genetic sequences. For example, different resistances (e.g., resistance values) may represent A, C, G, T, and/or U. In some examples, resistance of the memory cells may be programmed to represent a "don't care" value. While reference is made to programming resistance values to memory cells, it is understood that programming resistance values results in programming corresponding conductance values to memory cells as conductance (G)=1/resistance (R). Accordingly, references to programming resistance values and conductance values may be used interchangeably herein.

In some examples, the memory cells may be programmed by providing appropriate voltages to the word lines and/or bit lines. In some examples, values to be programmed to the memory cells may be converted from digital signals to analog signals by digital-to-analog converters (DACs) 114. In some examples, outputs from the memory array 110 may be converted to digital signals utilizing the analog-to-digital converters (ADCs) 115. Although the DACs 114 and ADCs 115 are illustrated as being coupled directly to the memory array 110, it some embodiments the DACs 114 and/or ADCs 115 may be coupled to the memory array 110 via the sensing circuitry 111, the row decoder 108, or the column decoder 112. Further, although not shown in FIG. 1, in some examples, some or all of the DACs 114 and/or ADCs 115 may be coupled between the memory array 110 and/or sense circuitry 111 and I/O circuitry 107.

In some embodiments, the various components of the memory device 103 outside the memory array 110, such as control circuitry 105, row decoder 108, and column decoder 112 may be shared by multiple memory arrays 110 and/or banks 116. In other embodiments, memory device 103 may include multiple ones of various components for the memory arrays 110 and/or banks 116. For example, in some embodiments, each bank 116-1 and 116-2 may be associated with different row decoders 108 and column decoders 112.

According to embodiments of the present disclosure, the memory device 103 may be used to implement a Bloom filter. A Bloom filter compares a pattern to a dataset and provides a result indicating whether the dataset includes the pattern (e.g., there is a match). Results from Bloom filters do not include false negatives, but may provide false positives. That is, if the Bloom filter indicates the pattern is not located in the dataset (e.g., negative), the pattern is absolutely not located in the dataset. However, if the Bloom filter indicates one or more locations where the pattern is found in the dataset (e.g., positive), the data at those locations must be analyzed to confirm the positive result.

The memory array 110 may be used to store one or more genetic sequences. For example, different portions of a reference genetic sequence (e.g., reference sequence) may be stored in memory cells along each bit line of the memory array 110. Each memory cell may be programmed with a resistance corresponding to the nucleotide at that location in the sequence. In some examples, each memory array 110 may store a different genetic sequence. In some examples, each bank 116 may store a different genetic sequence.

The memory array 110 may receive another genetic sequence, such as a read acquired from a sample. In some examples, each word line may be provided a voltage corresponding to a nucleotide at that location in the read. Utilizing the memory device 103 as a Bloom filter, the read may be compared to all of the sequences (or portions thereof) stored in one or more memory arrays 110 and/or banks 116 in parallel. The Bloom filter may indicate whether any of the portions of the sequence or sequences do not match and/or potentially match the read.

While the positive results of the Bloom filter may need confirmation (e.g., via additional analysis), the ability to definitively eliminate non-matches and compare the read to multiple portions of a reference sequence and/or multiple reference sequences in parallel may reduce the computation time required for determining where reads align.

Figure 2:
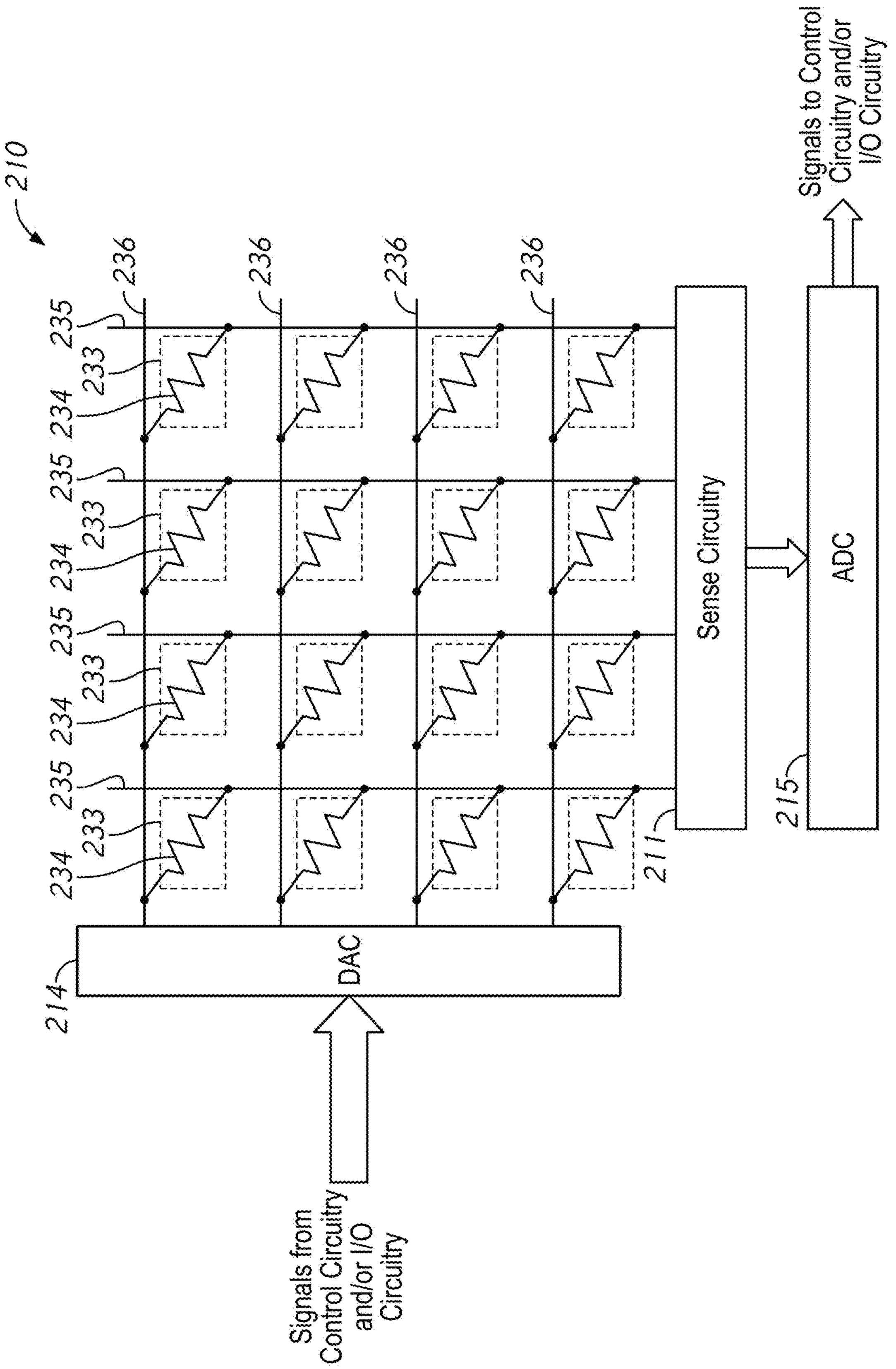
FIG. 2 illustrates a portion of a memory array in accordance with a number of embodiments of the present disclosure.

FIG. 2 illustrates a portion of a memory array in accordance with a number of embodiments of the present disclosure. The memory array 210 includes memory cells 233. The memory cells 233 are coupled to sense lines 235 and access lines 236, organizing the memory cells 233 in columns and rows, respectively. In some examples, memory array 210 may be included in memory array 110. Additional circuitry coupled to memory array 210 is also shown in FIG. 2, such as sense circuitry 211, DACs 214, and ADC 215. In some examples, sense circuitry 211 may be included in sense circuitry 211, DACs 214 may be included in DACs 114, and/or ADC 215 may be included in ADCs 114.

In some examples, such as the one shown in FIG. 2, the memory cells 233 may be resistive memory cells. The resistive memory cells 233 may include terminals that couple the memory cells 233 to the sense lines 235 and the access lines 236. The terminals of the memory cells 233 may be coupled to each other via a resistive element 234. The resistive element 234 may be a resistance variable material (e.g., a material programmable to multiple different resistance states, which may represent multiple different data states, such as different nucleotides) such as, for example, a transition metal oxide material, or a perovskite including two or more metals (e.g., transition metals, alkaline earth metals, and/or rare earth metals). Other examples of resistance variable materials that may be included in the storage element of resistive memory cells 233 may include various materials employing trapped charges to modify or alter conductivity, chalcogenides formed of various doped or undoped materials, binary metal oxide materials, colossal magnetoresistive materials, and/or various polymer based resistive variable materials, among others. Embodiments are not limited to a particular resistance variable material or materials. In various instances, the conductance of the memory cells 233 may be programmed by programming the resistive element 234. For instance, control circuitry of a memory device can program the resistive element 234. Actions performed by a memory device, the memory array 210, the memory cells 233 sense circuitry 211, DACs 214, and/or ADCs 215 may be said to be performed by or caused by control circuitry of the memory device (e.g., control circuitry 105).

As described herein, the memory array 210 and/or banks of the memory array 210 may be used to implement a Bloom filter. The memory array 210, or a portion thereof, may generate a Bloom filter output responsive to receipt of an input. The output can be generated using the resistance of the memory cells 233 and the input to the memory array 210. The resistive elements 234 can be programmed by providing inputs via the sense lines 235 and the access lines 236. Bloom filter operations of the memory array 210 may be performed by providing inputs through one of the sense lines 235 or the access lines 236.

In some examples, the inputs may be provided by sense lines 235 and/or the access lines 236. The inputs may be voltage inputs. In some examples, the inputs may be provided by DACs 214. The inputs provided by the DACs 214 may be based, at least in part, on control signals received from control circuitry (e.g., control circuitry 105) and/or signals provided from I/O circuitry (e.g., I/O circuitry 107).

In some examples, the outputs may be provided via the sense lines 235 or the access lines 236. In some examples, the outputs can be interpreted as current signals by the sense circuitry 211. The outputs can be provided to the ADCs 215. In some examples, the sense circuitry 211 may receive a current from each access line 236 and output a voltage, but in other examples, the sense circuitry 211 may provide a current for each access line 236 to the ADCs 215. In these examples, the ADCs 215 may receive a current and can output a voltage corresponding to each access line 236 and provide a corresponding output (e.g., a voltage). In some examples, the output from the ADCs 215 may be stored in registers (not shown) of a memory device (e.g., memory device 103), another array of the memory device, provided to control circuitry of the memory device, and/or provided to I/O circuitry of the memory device. In some examples, the outputs and/or data based on the outputs may be provided to a device external to the memory device, such as host 102.

Although the memory cells 233 are depicted as resistive memory cells with resistive elements 234, the present disclosure is not limited to this particular type of memory cell. For example, DRAM transistor memory cells operated in a sub-voltage threshold regime may be used.

Figure 3:
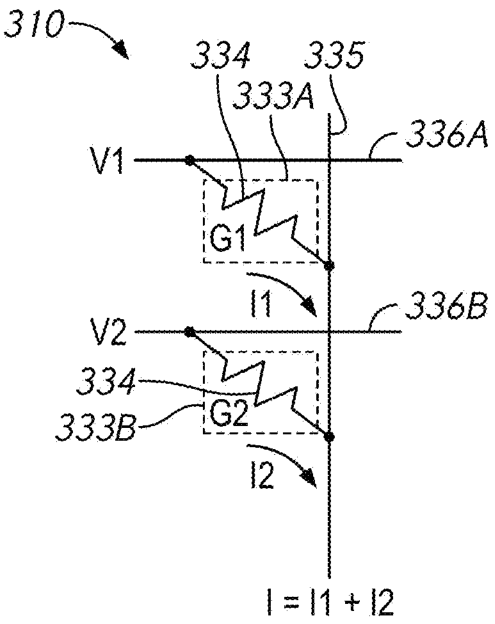
FIG. 3 illustrates a portion of a memory array in accordance with a number of embodiments of the present disclosure.

FIG. 3 illustrates a portion of a memory array in accordance with a number of embodiments of the present disclosure. The memory array 310 includes memory cells 333. The memory cells 333 are coupled to sense lines 335 and access lines 336. In some examples, memory array 310 may be included in memory array 110 and/or memory array 210.

In some embodiments, to implement a Bloom filter, the memory array 310 may act as a multiply-accumulator (MAC). A resistive element 334 of each memory cell 333 may be programmed to have a desired resistance (R). As used herein, the terms resistance and resistance values are used interchangeably. Voltage (V) inputs may be provided along each access line 336. As used herein, the terms voltage and voltage values are used interchangeably. The resulting current through each memory cell 333 due to the application of the voltage inputs is provided to a sense line 335, which may provide a current output. The voltage inputs may be provided by DACs, such as DACs 114 and/or 214 in some examples. The current output may be provided to sense circuitry such as sense circuitry 111 and 211 in some examples.

In the example shown in FIG. 3, a voltage V1 is provided along access line 336A to a memory cell 333A having a conductance G1 and a voltage V2 is provided along access line 336B to a memory cell 333B having a conductance G2. As is understood in the art, the conductance of the memory cells 333 may be based on the resistance of resistive elements 334. The resulting current I1 through memory cell 333A is equal to V1*G1. Current I1 is provided to sense line 335. The resulting current I2 through memory cell 333B is equal to V2*G2 is also provided to sense line 335. The total current I on sense line 335 is the sum of I1 and I2. Thus, the total current is the sum of the multiplication operations at each of the memory cells 333 along the sense line 335 to implement the multiply-accumulate operation:

$$I = I1 + I2 = (V1 \times G1) + (V2 \times G2) \quad \text{Equation 1}$$

Thus, the total current for a sense line 335 is a sum of all the products of the voltage values along the access lines 336 and the conductance values of the memory cells 333 along the corresponding sense line 335. As is understood in the art, if the states of the memory cells 333 are represented as resistance (R), where G=1/R, the total current I would be the sum of division operations:

$$I = I1 + I2 = (V1 \div R1) + (V2 \div R2) \quad \text{Equation 2}$$

Although only one sense line 335 and two memory cells 333 are shown in FIG. 3, the voltage inputs along access lines 336 may be provided to memory cells along multiple sense lines simultaneously, or near simultaneously. Multiple sense lines may provide outputs simultaneously or near simultaneously. Thus, multiple multiply-accumulate operations may be performed in parallel in the memory array 310.

According to embodiments of the present disclosure, the resistance levels and voltage levels can represent data, such as data that corresponds to a nucleotide of a genetic sequence. For example, each nucleotide type A, C, G, T, and/or U may correspond to a different level (e.g., value) of resistance (e.g., conductance) and/or voltage. A genetic sequence may be stored in one or more memory cells 333 along a sense line 335 of the memory array, and another genetic sequence may be provided as an inputs along access lines 336. The stored genetic sequence may be stored as a set of resistances, and the input genetic sequence may be provided as a set of voltages. This may result in a current output along sense line 335. The resulting current may be used to determine whether the input genetic sequence possibly matches the genetic sequence stored in the memory cells 333 stored along sense line 335.

Figure 4:
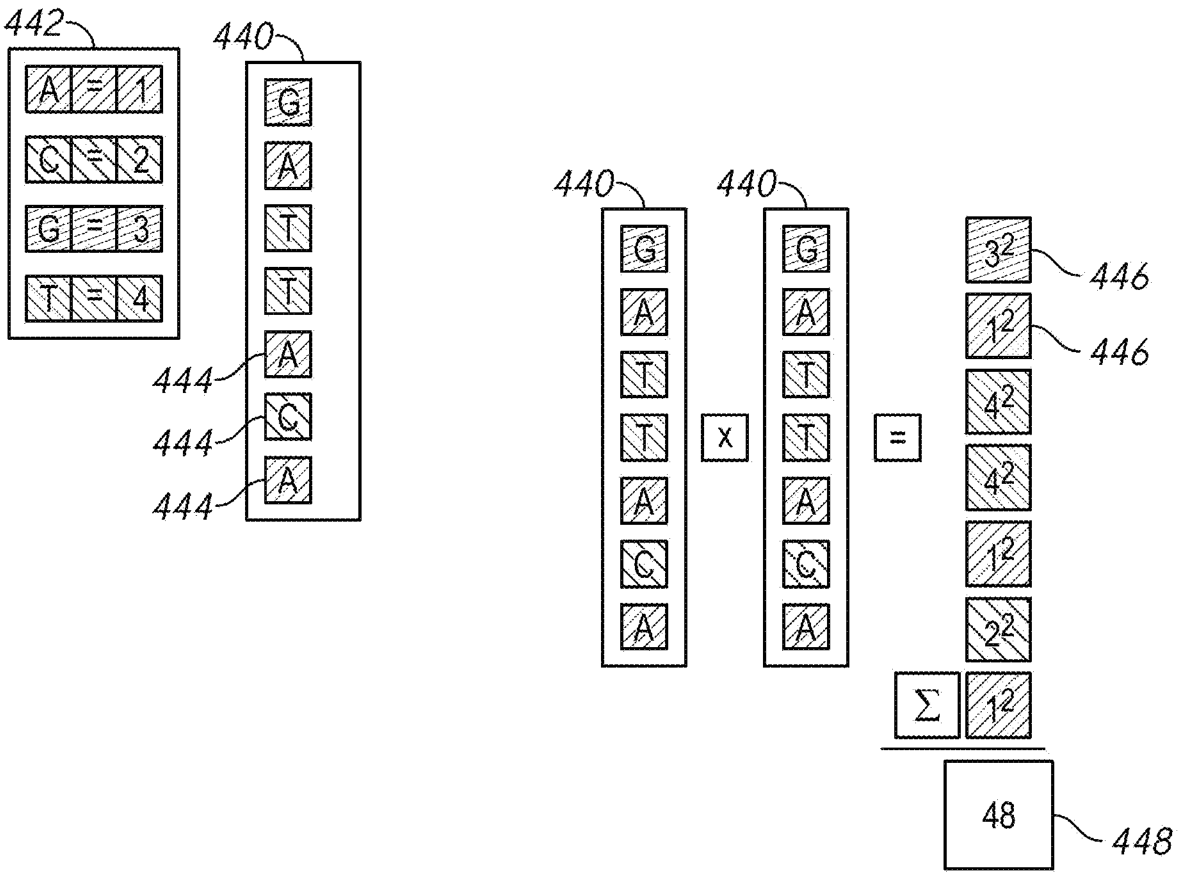
FIG. 4 illustrates an example of a multiply-accumulate operation for a genetic sequence in accordance with a number of embodiments of the present disclosure.

FIG. 4 illustrates an example of a multiply-accumulate operation for a genetic sequence in accordance with a number of embodiments of the present disclosure. Genetic sequence 440 includes multiple nucleotides 444. In this example, genetic sequence 440 is a DNA sequence that includes nucleotides A, C, G, and T, but in other examples, genetic sequence 440 may be an RNA sequence or other genetic sequence. Each nucleotide type is assigned a different resistance/conductance value and a different voltage value compared to the other nucleotide types. In the simple example shown in FIG. 4, each nucleotide type is assigned a same value for both resistance/conductance and voltage as shown in legend 442. In other examples, each nucleotide type may be assigned different values for resistance and voltage. Further, although values 1, 2, 3, and 4 are used in the present example, other values may be used in other examples. For example, prime numbers (e.g., 1, 3, 5, and 7) may be used.

The genetic sequence 440 is multiplied with itself on a nucleotide-by-nucleotide basis. In the example shown in FIG. 4, the multiplication operations are G×G (3×3), A×A (1×1), T×T (4×4), T×T (4×4), A×A (1×1), C×C (2×2), and A×A (1×1). The voltage assigned to each nucleotide 444 of sequence 440 is multiplied with the conductance assigned to the corresponding nucleotide 444 of sequence 440 to provide a resulting current value 446 for each nucleotide 444. The resulting currents for all of the nucleotides 444 in the sequence 440 are then summed (e.g., accumulated) to provide a total current 448. The total current in the example shown in FIG. 4 is 48 (e.g., uAmp, mAmp, etc.).

The resulting total current 448 indicates an expected total current (e.g., target value) from a multiply-accumulate operation when an input genetic sequence matches a genetic sequence stored along a sense line (e.g., sense line 235, 335) of a memory array (e.g., memory array 110, 210, 310). When the resulting current of a sense line does not match the target value for an input genetic sequence, the genetic sequence stored along the sense line may be definitively determined not to be a match of the input sequence. When the resulting current of the sense line does match the expected resulting current for the input sequence, it indicates a potential match. The input sequence provided to the memory array and the genetic sequence stored along the sense line of the memory array may be compared by another technique to confirm the match. Thus, a memory array performing multiply-accumulation operations may act as a Bloom filter.

Figure 5:
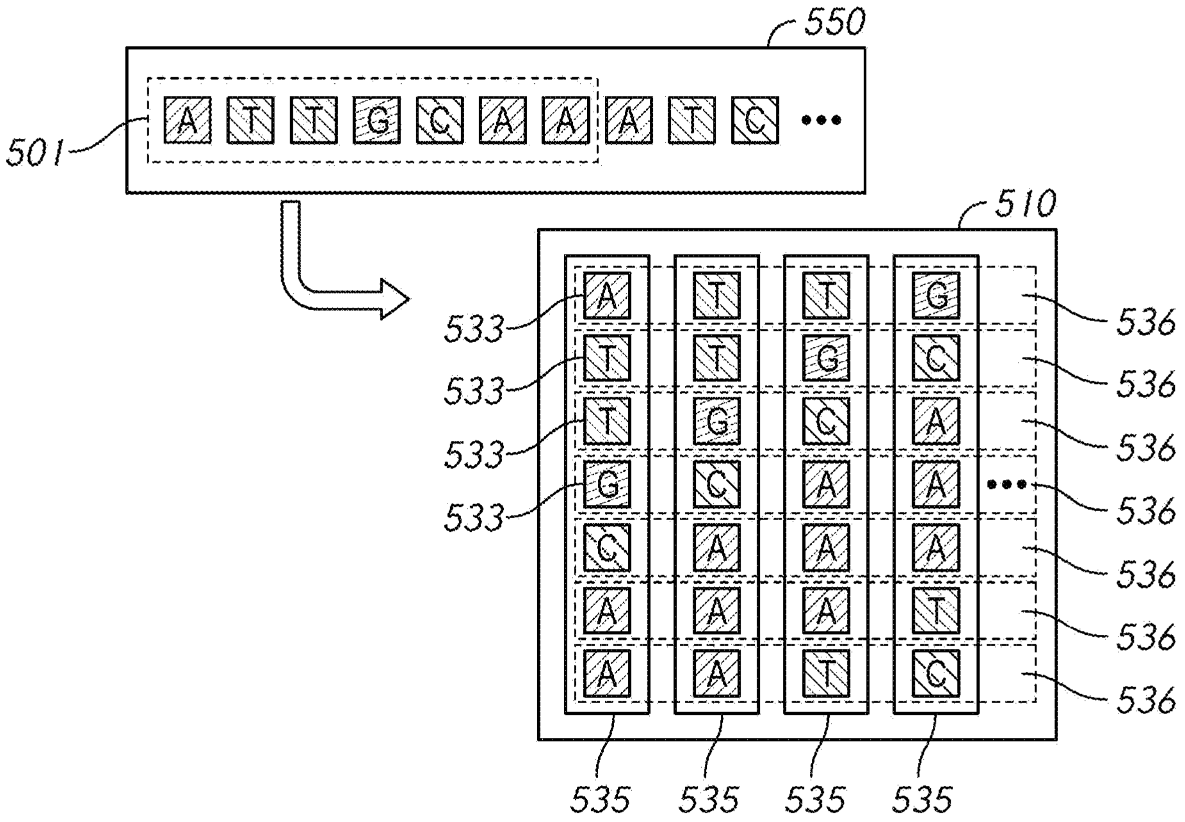
FIG. 5 illustrates an example of storing a reference sequence in a memory array in accordance with a number of embodiments of the present disclosure.

FIG. 5 illustrates an example of storing a reference sequence in a memory array in accordance with a number of embodiments of the present disclosure. The memory array 510 may be included in memory array 110, 210, and/or 310 in some embodiments. The memory array 510 may include memory cells 533 along sense lines 535 and access lines 536. Memory cells 533 may be implemented by memory cells 233 and/or 333 in some examples. Sense lines 535 may be implemented by sense lines 235 and/or 335 in some examples. Access lines 536 may be implemented by access lines 236 and/or 336 in some examples. While for illustration, memory array 510 is shown including seven access lines 536, it is understood that memory array 510 may include any number of access lines 536. Furthermore, although only four sense lines 535 are shown in FIG. 5, memory array 510 may include any number of sense lines 535. While each memory cell 533 may include a resistive element (e.g., resistive element 234 and/or 334) or other element capable of performing a multiply-accumulate operation, for ease of illustration, the memory cells 533 are illustrated as blocks with letters indicating the nucleotide stored in the memory cell 533 (e.g., based on a resistance programmed in the memory cell 533).

A reference sequence 550 may be provided to the memory array 510 (e.g., via control circuitry 105 and/or I/O circuitry 107) for storage in the memory array 510. A portion of the reference sequence 550 may be stored along each sense line 535. In some examples, a sliding window 501 having a length of the sense line 535 may be progressed along the reference sequence 550, and each sense line 535 may store the portion of the reference sequence 550 located within the sliding window 501 at a particular position in the progression. In some examples, such as the one shown in FIG. 5, the sliding window 501 may be progressed one nucleotide at a time, and the portion of the reference sequence 550 stored in a sense line 535 may be shifted by one nucleotide compared to the adjacent sense line 535. However, the sliding window 501 may be progressed by more than one nucleotide in other examples.

In some examples, the sliding window 501 may be progressed until the end of the reference sequence 550. If the reference sequence 550 is long enough such that the memory array 510 "runs out" of sense lines 535 to store portions of the reference sequence 550, the remaining portions of the reference sequence 550 may be stored in another memory array. In some examples, the remaining portions may be stored in a memory array of a same bank as memory array 510. In some examples, the remaining portions may be stored in a memory array of a different bank as memory array 510.

While one reference sequence 550 is shown in FIG. 5, in some examples, multiple reference sequences may be stored in memory array 510. In some examples, different reference sequences may be stored in different memory arrays of a bank including memory array 510. In some examples, different banks may store different reference sequences. In some examples, how the reference sequence 550 is divided into portions, stored, and/or shifted in the memory array 510 (or across multiple memory arrays) is performed based on control signals provided by control circuitry, such as control circuitry 105. In some examples, the control signals may be based, at least in part, on instructions/commands provided by a host, such as host 102.

In some embodiments, once the reference sequence 550 is stored in memory array 510 based, at least in part, on resistance values of the memory cells 533, reads may be provided to memory array 510 for comparison to the reference sequence 550.

Figure 6:
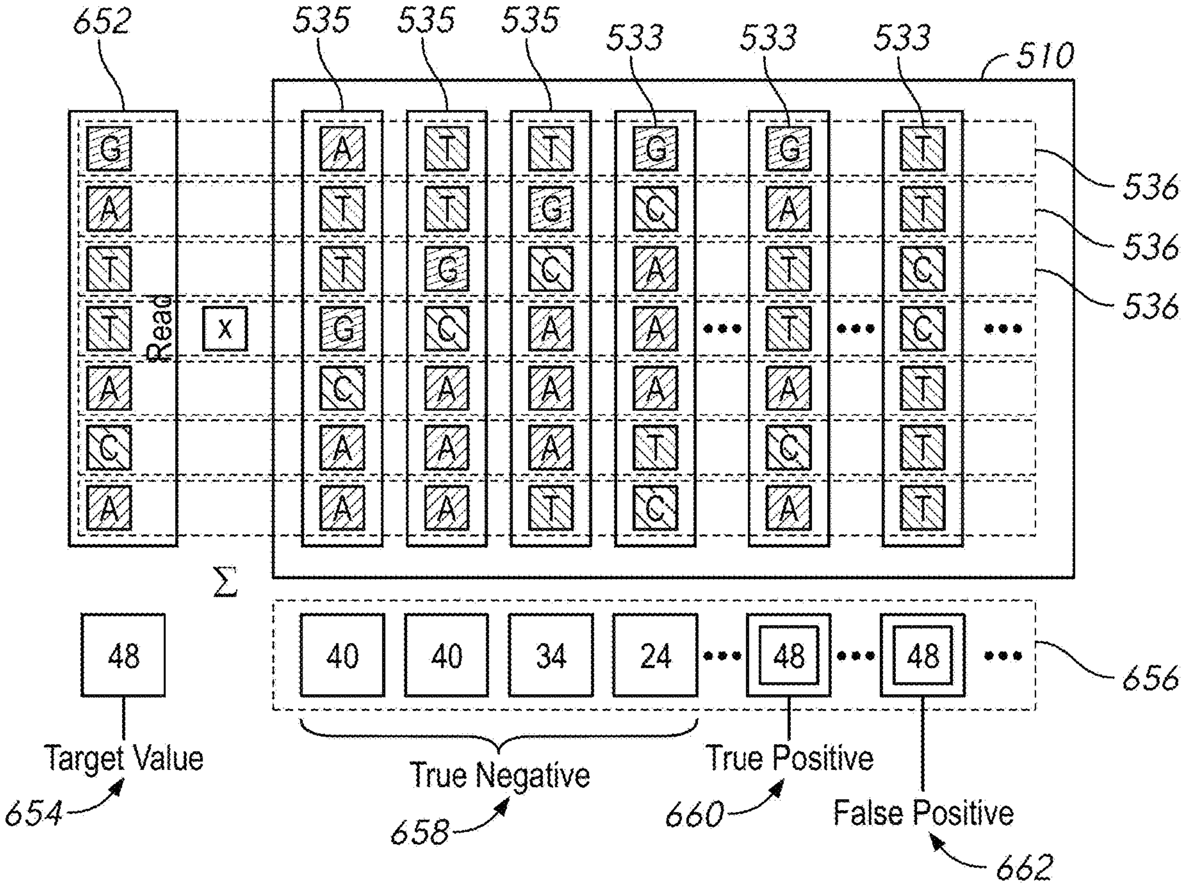
FIG. 6 illustrates an example of comparing reads to reference sequences stored in the memory array shown in FIG. 5 in accordance with a number of embodiments of the present disclosure.

FIG. 6 illustrates an example of comparing reads to reference sequences stored in the memory array shown in FIG. 5 in accordance with a number of embodiments of the present disclosure. In some examples, read 652 may be provided as voltages along access lines 536 (e.g., via DACs 114, 214). For ease of illustration, rather than voltage levels along the access lines 536, read 652 is illustrated as blocks with letters indicating the nucleotide represented by the voltage level. In some examples, data indicating the voltages to be provided for the read 652 may be stored in a register of the memory device including memory array 510. In some examples, the data indicating the voltages to be provided for the read 652 may be provided in a different memory array and/or memory bank of the memory device. In some examples, the data indicating the voltages to be provided for the read 652 may be provided by control circuitry and/or I/O circuitry of the memory device (e.g., control circuitry 105 and I/O circuitry 107).

In some examples, the read 652 may be the same length as the portions of the reference sequence 550 stored along each sense line 535. In some examples, the length of the portions of the reference sequence 550 stored along each sense line 535 (e.g., the length of the sliding window) may be based, at least in part, on an expected shortest read generated by a sequencing system. In some examples, read 652 may be "padded" by values for voltages that indicate a "don't care" and/or that will not affect the results of the multiply-accumulate operation.

The read 652 may be provided to all of the portions of the reference sequence 550 along each of the sense lines 535 simultaneously or near simultaneously. The voltage corresponding to the nucleotide along each access line 536 may pass through the corresponding memory cells 533 of the access line 536, generating a current. The current may be based on the voltage provided to the access line 536 and the resistance/conductance value programmed to each memory cell 533. The current through each memory cell 533 may be provided to the corresponding sense line 536. The currents along the sense line 536 may be summed, thus a multiply-accumulate operation may be performed along each sense line 536. The sum of the currents of the memory cells 533 may be provided from the sense lines 536 to sense circuitry (e.g., sense circuitry 111, 211). In some examples, the sense circuitry may provide current outputs for analysis. In some examples, the sense circuitry may provide the sensed currents to ADCs (e.g., ADCs 115, 215) that may convert the currents into digital signals representing the currents as an output.

For ease of illustration, the outputs 656 associated with each of the sense lines 536 are illustrated as boxes with numerical values reflecting the result of the multiply-accumulate operations of the read 652 with the portions of the reference sequence 550 based on the values provided in legend 442. As described with reference to FIG. 4, the target value 654 (e.g., expected value) of the read 652 multiplied and summed against itself is 48. Several outputs 656 have values that are not equal to 48. These outputs are true negatives 658. In some embodiments, there may be no mechanism for the MAC of the Bloom filter as disclosed herein to provide a false negative. Accordingly, the portions of the reference sequence 550 stored along sense lines 535 associated with the true negatives 658 may be ignored or discarded as potential matches for the read 652.

While there may not be false negatives, there may be multiple combinations of conductance and voltage values that when multiplied and summed equal 48, which may lead to false positives. True positive 660 output correctly indicates a portion of the reference sequence 550 of a sense line 535 matches the read sequence 652. However, false positive 662 also equals 48, even though the portion of the reference sequence 550 stored along the associated sense line 535 does not match read sequence 652. Accordingly, outputs 656 that match the target value 654 may be further analyzed prior to confirming a potential alignment location of the read 652 in the reference sequence 550. In some examples, the portions of the reference sequence 550 stored along the sense lines 535 having positive results (e.g., outputs 656 match the target value 654) may be compared to the read 652 on a nucleotide-by-nucleotide basis. In some examples, other comparison techniques may be used. In some examples, this additional analysis may be performed on the memory device, such as by pattern matching circuitry, which may include a content addressable memory and/or one or more comparator circuits. In some examples, the portions of the reference sequence 550 and the read 652 may be provided to an external device, such as host 102, which may perform the additional analysis. This additional analysis may filter out false positive 662 and retain true positive 660.

Once confirmed, the true positive 660 indicates that the read sequence 652 may align to the reference sequence 550 at the location of the reference sequence 550 along the corresponding sense line 535. Because it is known which portion of the reference sequence 550 is stored along each sense line 535, it can be determined where in the reference sequence 550 read 652 may be aligned to. In some examples, such as when the memory confirms the true positive 660, the memory may provide an output indicating a location in the reference sequence 550 that the read 652 aligns to (e.g., alignment location). The output may be stored in a register or memory array of the memory device, such as memory device 103. In some examples, the output may be provided to an external device, such as host 102. In other examples, such as when the external device performs the additional analysis, the alignment location may be provided to the memory device or another memory device for storage and/or used in further processing for recombining all of the analyzed reads into a longer sequence (e.g., a sequence of the sample from which the reads were acquired).

While positive results 660, 662 may require additional computation time to confirm, the ability of the Bloom filter implemented by memory array 510 to compare the read 652 to many portions of the reference sequence 550 in parallel and definitively eliminate portions that are not matches, the overall computation time for aligning the read 652 to the reference sequence 550 (or determining the read 652 does not align to the reference sequence 550 when there are no matches) may be less.

While read 652 is shown as being compared against multiple portions of a reference sequence 500 in parallel in a single memory array 510 in FIG. 6, in some examples, read 652 may be provided in parallel to multiple memory arrays and/or banks of memory arrays in parallel. Each memory array and/or bank may include one or more reference sequences. In some examples, reads may be provided to the memory device in series (e.g., one read at a time is compared to the reference sequence(s) in the memory array(s)). However, in some examples, multiple reads may be compared to reference sequences in parallel. For example, different reads may be provided to different memory arrays and/or banks in parallel.

As described with reference to FIG. 6, any output 656 that does not match the target value 654 is discarded or ignored. However, a genomic sample from which reads are obtained does not typically have a sequence that exactly matches a reference sequence, even if the genomic sample is a same organism. For example, mutations may cause changes in the sequence between the sample and the original organism from which the reference sequence was obtained (e.g., alpha, beta, delta, and omicron variants and sub-variants thereof for COVID-19). Additionally, the process of obtaining reads from the sample is not perfect. Some reads may include one or more of a mismatched nucleotide (e.g., a transcription error), a deletion of a nucleotide and/or an insertion of a nucleotide.

In some applications, if only outputs 656 that exactly match the target value 654 are retained/further analyzed, the Bloom filter may not tolerate mutations or read errors. This may lead to an unacceptable number of reads marked as not aligning to the reference sequence. To increase error tolerance, in some embodiments, true negatives 658 with values within a range of the target value 654 may be retained/further analyzed. For example, true negatives 658 having a value within +/−2 of the target value 654 (e.g., between 46 and 50) may also be analyzed as a possible "close match." Further analysis performed by the memory and/or host may determine whether the close matches are false close matches or "true" close matches due to a mutation and/or read error. The width of the range may be based, at least in part, on a length of the read 652 and/or a desired error tolerance. Increasing the error tolerance in some cases may increase computation time as it may lead to additional portions of the reference sequence 550 requiring additional analysis (e.g., nucleotide-by-nucleotide comparison and/or additional processing to determine error/mutation type).

In some applications, particularly when the Bloom filter is implemented by analog components, some margin of error around the target value 654 may be provided for outputs 656 that are analyzed as potential positives. For example, variations in resistances of memory cells 533 and/or sense circuitry may cause variations in the results of the multiply-accumulate operation. The variations may be due to processing variations, temperature, atomic/ion migration in components, and/or other factors. The margin of error may be based, at least in part, on material properties of the memory, operational properties of the memory, environmental factors, or a combination thereof.

Figure 7:
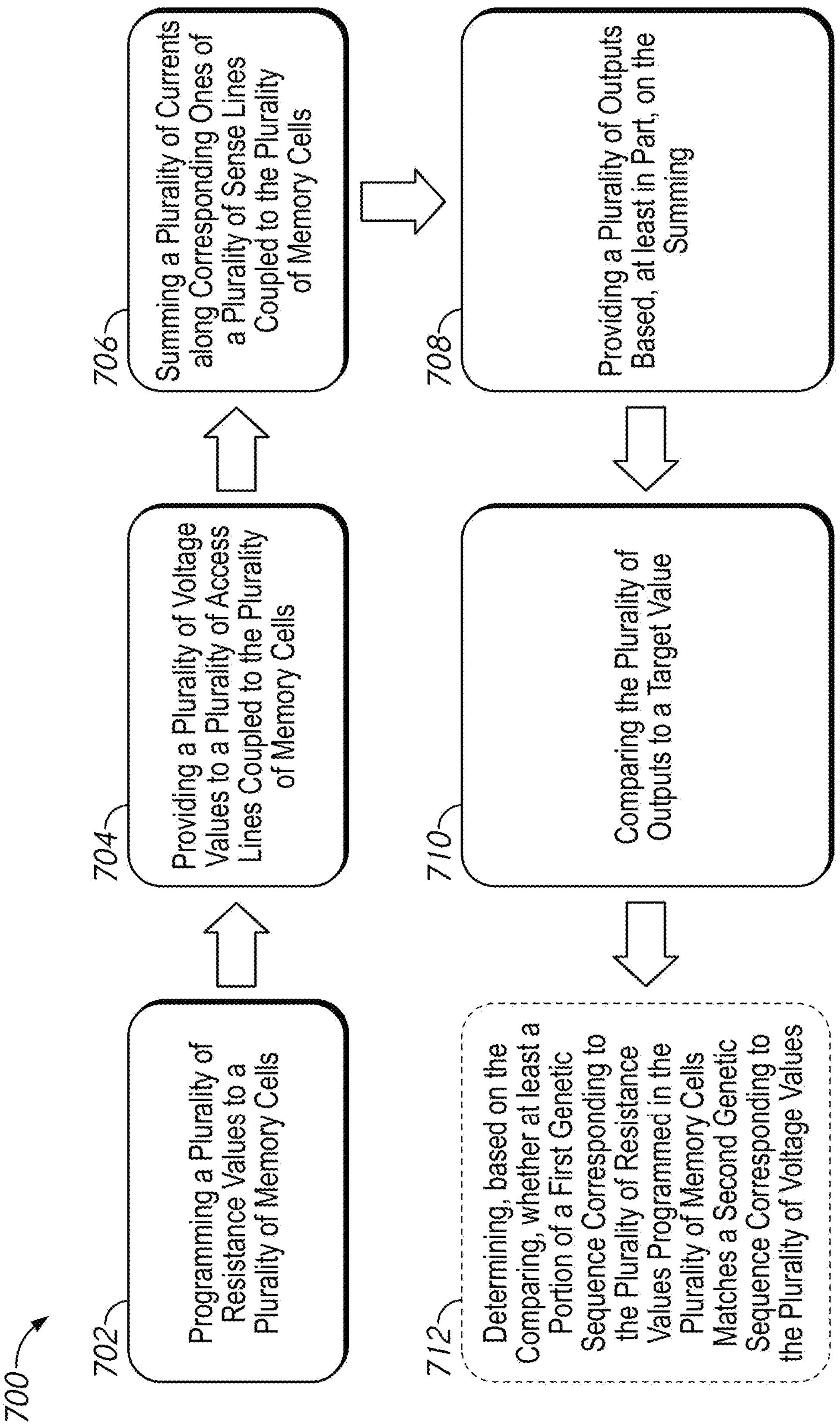
FIG. 7 is a flowchart of a method in accordance with a number of embodiments of the present disclosure.

FIG. 7 is a flowchart of a method in accordance with a number of embodiments of the present disclosure. In some examples, the method 700 may be performed at least in part by a computing system such computing system 100 shown in FIG. 1. In some examples, the method 700 may be performed at least in part by a memory array, such as memory array 110, 210, 310, and/or 510.

At block 702, "programming a plurality of resistance values to a plurality of memory cells" may be performed. In some examples, the plurality of resistance values may correspond to nucleotide types (e.g., A, C, G, T, and U). In some examples, the programming may be performed, at least in part, by control circuitry, such as control circuitry 105. In some examples, programming of the plurality of resistance values may be based, at least in part, on a first genetic sequence. In some examples, the first genetic sequence may be a reference sequence.

At block 704, "providing a plurality of voltage values to a plurality of access lines coupled to the plurality of memory cells." In some examples, the plurality of voltage values correspond to the nucleotide types. In some examples, the plurality of voltage values may be based, at least in part on a second genetic sequence. In some examples, the second genetic sequence may be a read sequence. In some examples, the voltage values may be provided by one or more DAC, such as DAC 114, 214. In some examples, the DAC may provide the input responsive to signals received from the control circuitry. In examples including a DAC, providing the plurality of voltage values may include converting a digital input into the plurality of voltage values.

At block 706 "summing a plurality of currents along corresponding ones of a plurality of sense lines coupled to the plurality of memory cells" may be performed. In some examples, the plurality of currents may be functions of the plurality of voltage values and corresponding ones of the plurality of resistance values of the plurality of memory cells along corresponding ones of the plurality of sense lines, as described with reference to FIG. 3 and Equations 1-2.

At block 708, "providing a plurality of outputs based, at least in part, on the summing" may be performed. In some examples, the outputs may be provided from the sense lines to sense circuitry, such as sense circuitry 111, 211. In some examples, the outputs may be provided from the sense circuitry to an ADC, such as ADC 115, 215. In some examples, the outputs may be provided from the ADC. In these examples, providing the plurality of outputs may include converting the summed plurality of currents from an analog signal to a digital signal. In some examples, method 700 may further include storing the outputs, such as in a register or a memory array of the memory device.

At block 710, "comparing the plurality of outputs to a target value" may be performed. In some examples, the comparing may be performed by a memory device, such as memory device 103. In some examples, the comparing may be performed by a host, such as host 102. In some examples, the results of the comparing may be stored, such as in the memory device or another device.

Figure 8:
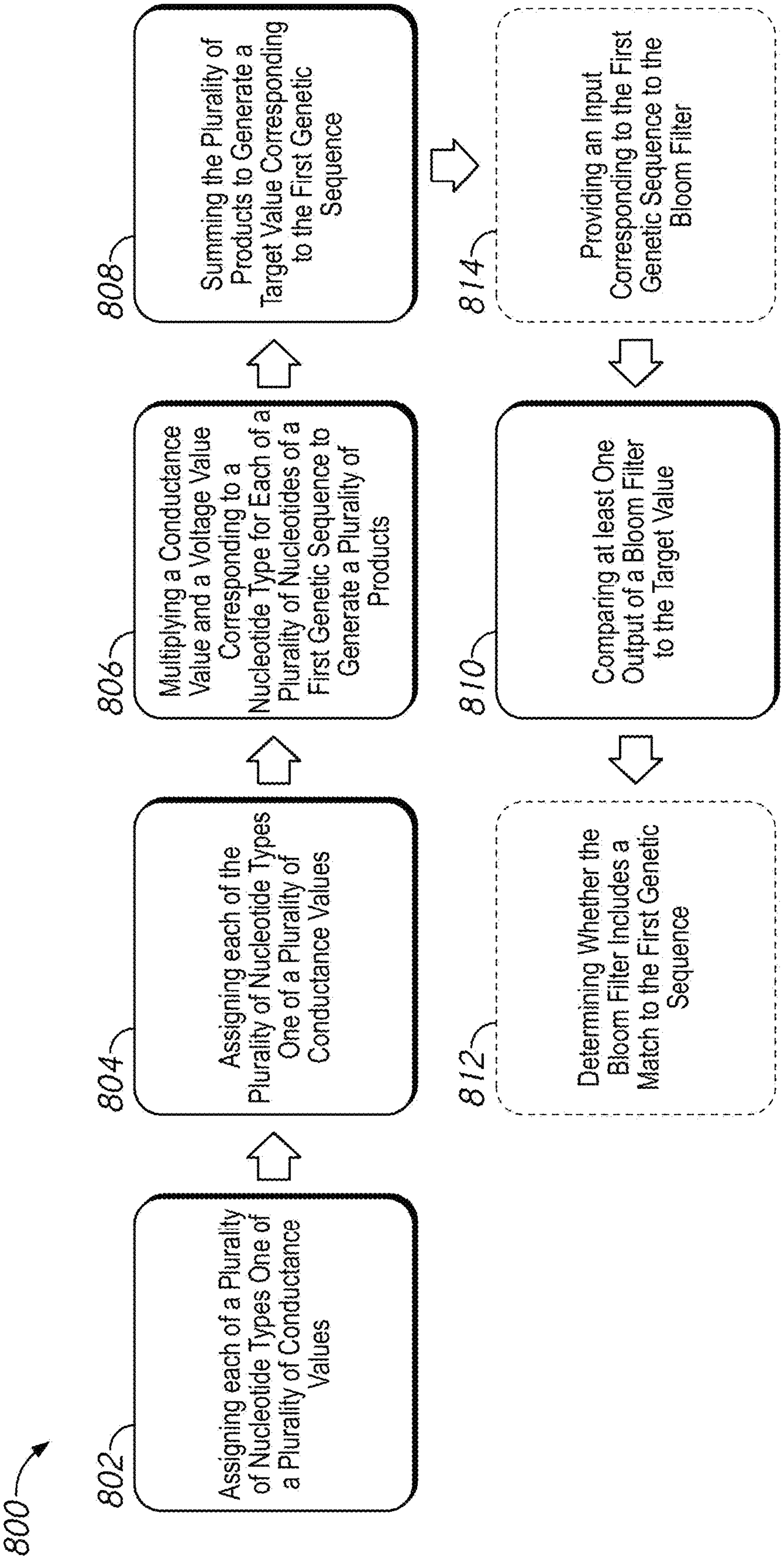
FIG. 8 is a flowchart of a method in accordance with a number of embodiments of the present disclosure.

In some embodiments, method 700 may further include "determining, based on the comparing, whether at least a portion of a first genetic sequence corresponding to the plurality of resistance values programmed in the plurality of memory cells matches a second genetic sequence corresponding to the plurality of voltage values" as indicated by block 712. In some examples, a potential match may be determined when at least one of the plurality of outputs matches the target value. In some examples, a potential match may be determined when at least one of the plurality of outputs is within a range of the target value. As discussed previously, a range may be used to increase tolerance for mutations and errors in the reads in some applications FIG. 8 is a flowchart of a method in accordance with a number of embodiments of the present disclosure. In some examples, the method 800 may be performed at least in part by a computing system such computing system 100 shown in FIG. 1. In some examples, the method 800 may be performed at least in part by a memory array, such as memory array 110, 210, 310, and/or 510.

At block 802, "assigning each of a plurality of nucleotide types one of a plurality of conductance values" may be performed.

At block 804, "assigning each of the plurality of nucleotide types one of a plurality of voltage values" may be performed.

At block 806, "multiplying a conductance value and a voltage value corresponding to a nucleotide type for each of a plurality of nucleotides of a first genetic sequence to generate a plurality of products" may be performed.

At block 808, "summing the plurality of products to generate a target value corresponding to the first genetic sequence" may be performed. An example of performing blocks 802-808 is shown and described in reference to FIG. 4.

At block 810, "comparing at least one output of a Bloom filter to the target value" may be performed. For example, as shown and described with reference to FIG. 6. In some examples, when the at least one output of the Bloom filter is equal to the target value, method 800 may further include comparing the first genetic sequence to a second genetic sequence corresponding to the at least one output on a nucleotide-by-nucleotide basis. The comparing may be performed by a memory device, such as memory device 103 and/or a host, such as host 102. In some examples, when the at least one output of the Bloom filter is not equal to the target value, the at least one output may be ignored or discarded.

In some examples, the Bloom filter is configured to store at least one reference sequence. In some examples, the at least one reference sequence includes a genetic sequence of a virus or a bacterium. In some examples, the first genetic sequence corresponds to a read sequence acquired from a biological sample. In some examples, blocks 806, 808, and 810 may be repeated for each of a plurality of genetic sequences (e.g. multiple read sequences).

At block 812, based on the comparing "determining whether the Bloom filter includes a match to the first genetic sequence" may be performed.

As indicated by block 814, in some examples, method 800 may further include "providing an input corresponding to the first genetic sequence to the Bloom filter." In some examples, the at least one output is based, at least in part, on the input.

In some examples, the Bloom filter is implemented by a memory array configured to store a second genetic sequence in a plurality of memory cells. In some of these examples, method 800 may further include programming a plurality of resistive elements of the plurality of memory cells with the plurality of conductance values corresponding to the second genetic sequence. In some of these examples, method 800 may further include storing a plurality of portions of the second genetic sequence along corresponding ones of a plurality of sense lines of the memory array. In some examples each of the plurality of sense lines includes a portion of the second genetic sequence shifted by at least one nucleotide. For example, as indicated by sliding window 501 shown in FIG. 5.

Although the examples herein describe storing one or more reference sequences in memory and providing reads to the memory for comparison, reads may also be stored in the memory. For example, one or more reads may be stored in a memory array, and one or more reference sequences (or portions thereof) may be provided for comparison to the reads in the memory array. Thus, instead of a read being compared to multiple portions of a reference sequence, multiple reference sequences, and/or a combination thereof in parallel, a reference sequence may be compared to multiple reads in parallel. Further, instead of different reads being provided in series, different reference sequences, permutations of the reference sequence, and/or portions thereof may be provided in series.

While the examples herein refer to determining "correct" locations of reads and/or alignment locations of reads for a reference sequence based on confirmed positive outputs of the Bloom filter, the locations within the reference sequence determined from the Bloom filter may be candidate locations (may also be referred to as estimated or potential locations) locations for the reads. Genomic sequences may include regions where patterns of nucleotides are repeated. Thus, there may be several perfect and/or close matches for locations in the reference sequence where a read may be aligned. The chance of multiple candidate locations increases as the length of the read decreases and/or the length of the reference sequence increases.

After positive results have been confirmed, the memory device, host, and/or other device may perform additional processing to "narrow down" the potential alignment locations of reads provided by the Bloom filter when there are multiple potential alignment locations. In some applications, this may be based on one or more probabilistic methods known in the art of genetic sequencing. However, by using parallel processing capabilities of memory arrays, such as resistive memory arrays, as disclosed herein, the overall computing time for aligning reads to reference sequences may be reduced.

Certain details set forth herein provide a sufficient understanding of examples of the disclosure. However, it will be clear to one having skill in the art that examples of the disclosure may be practiced without these particular details. Moreover, the particular examples of the present disclosure described herein should not be construed to limit the scope of the disclosure to these particular examples. In other instances, well-known circuits, control signals, timing protocols, and software operations have not been shown in detail in order to avoid unnecessarily obscuring the disclosure. Additionally, terms such as "couples" and "coupled" mean that two components may be directly or indirectly electrically coupled. Indirectly coupled may imply that two components are coupled through one or more intermediate components.

From the foregoing it will be appreciated that, although specific embodiments of the disclosure have been described herein for purposes of illustration, various modifications may be made without deviating from the spirit and scope of the disclosure. Accordingly, the scope disclosure should not be limited any of the specific embodiments described herein.

What is claimed is:

1. A method comprising:

summing a plurality of currents along corresponding ones of a plurality of sense lines coupled to a plurality of memory cells, wherein the plurality of currents are functions of a plurality of voltage values and corresponding ones of a plurality of resistance values of the plurality of memory cells along corresponding ones of the plurality of sense lines;

providing a plurality of outputs based, at least in part, on the summing; and comparing the plurality of outputs to a target value.

2. The method of claim 1, wherein the plurality of resistance values correspond to nucleotide types.

3. The method of claim 1, wherein the plurality of voltage values correspond to nucleotide types.

4. The method of claim 1, further comprising programming the plurality of resistance values to the plurality of memory cells.

5. The method of claim 1, further comprising providing the plurality of voltage values to a plurality of access lines coupled to the plurality of memory cells.

6. The method of claim 1, determining whether there is a potential match between the plurality of outputs and the target value.

7. The method of claim 6, wherein the potential match is determined when at least one of the plurality of outputs is within a range of the target value.

8. The method of claim 6, wherein the potential match indicates at least a portion of a first genetic sequence corresponding to the plurality of resistance values programmed in the plurality of memory cells matches a second genetic sequence corresponding to the plurality of voltage values.

9. The method of claim 1, further comprising storing the plurality of outputs.

10. The method of claim 1, further comprising storing results of the comparing.

11. A method comprising:

multiplying a conductance value and a voltage value corresponding to a nucleotide type for each of a plurality of nucleotides of a first genetic sequence to generate a plurality of products;

summing the plurality of products to generate a target value corresponding to the first genetic sequence; and comparing at least one output of a Bloom filter to the target value.

12. The method of claim 11, further comprising assigning each of a plurality of nucleotide types one of a plurality of conductance values.

13. The method of claim 11, further comprising assigning each of the plurality of nucleotide types one of a plurality of voltage values.

14. The method of claim 11, further comprising based on the comparing, determining whether the Bloom filter includes a potential match to the first genetic sequence.

15. The method of claim 11, further comprising providing an input corresponding to the first genetic sequence to the Bloom filter, wherein the at least one output is based, at least in part, on the input.

16. The method of claim 11, wherein the Bloom filter is implemented by a memory array configured to store a second genetic sequence in a plurality of memory cells.

17. The method of claim 16, further comprising programming a plurality of resistive elements of the plurality of memory cells with the plurality of conductance values corresponding to the second genetic sequence.

18. The method of claim 16, further comprising storing a plurality of portions of the second genetic sequence along corresponding ones of a plurality of sense lines of the memory array, wherein each of the plurality of sense lines includes a portion of the second genetic sequence shifted by at least one nucleotide.

19. The method of claim 11, further comprising when the at least one output of the Bloom filter is equal to or within a range of the target value, comparing the first genetic sequence to a second genetic sequence corresponding to the at least one output on a nucleotide-by-nucleotide basis.

20. The method of claim 11, further comprising when the at least one output of the Bloom filter is not equal to or not within a range of the target value, ignoring or discarding the at least one output.

* * * * *